United States Patent [19]
Yabutani et al.

[11] 4,093,743
[45] June 6, 1978

[54] NOVEL BENZOIC ANILIDE DERIVATIVE AND FUNGICIDE CONTAINING SAME

[75] Inventors: Kunihiro Yabutani, Izumi; Kenichi Ikeda, Toyonaka; Shigenori Hatta, Sakai; Tatsuo Harada, Kawachinagano, all of Japan

[73] Assignee: Nihon Nohyaku Co., Ltd., Tokyo, Japan

[21] Appl. No.: 814,714

[22] Filed: Jul. 11, 1977

[30] Foreign Application Priority Data

Jul. 12, 1976 Japan .................................. 51-82711
Jun. 20, 1977 Japan .................................. 52-73024

[51] Int. Cl.² ...................... A01N 9/20; C07C 103/76
[52] U.S. Cl. .................................. 424/324; 260/558 P
[58] Field of Search ..................... 424/324; 260/558 P

[56] References Cited

U.S. PATENT DOCUMENTS

| | | | |
|---|---|---|---|
| 3,937,840 | 2/1976 | Chiyomaru et al. | 424/324 |
| 3,969,510 | 7/1976 | Osieka et al. | 424/324 |
| 3,985,804 | 10/1976 | Chiyomaru et al. | 260/558 P |

Primary Examiner—Allen J. Robinson
Attorney, Agent, or Firm—Cushman, Darby & Cushman

[57] ABSTRACT o-Trifluoromethylbenzoic m'-isopropoxyanilide formed by the reaction between o-trifluoromethylbenzoic acid and m-isopropoxyaniline is very effective in controlling agricultural and horticultural plant diseases.

3 Claims, No Drawings

NOVEL BENZOIC ANILIDE DERIVATIVE AND FUNGICIDE CONTAINING SAME

This invention relates to o-trifluoromethylbenzoic m'-isopropoxyanilide represented by the structural formula (I)

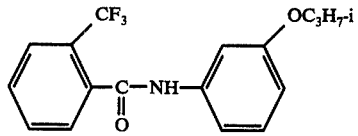

(I)

and to a method for producing same. Further, it relates to an agricultural and horticultural fungicide preparation containing as active ingredient the compound represented by the structural formula (I).

Though some of benzoic anilide derivatives are known as effective for controlling fungi (U.S. Pat. Nos. 3,969,510, 3,985,804 and 3,937,840), the compound of this invention has a distinguished preventive and exterminative effect on diseases of agricultural and horticultural crops, such as vegetable diseases, e.g. southern blight and damping-off; rust diseases of agricultural and horticultural crops, e.g. red spot of pear and apple, rust diseases of grape, chrysanthemum, wheat and barley; blossom blight of apple; white rot of Welsh onion, leaf rot of sugar beet, sheath blight of rice, and brown sclerotium disease of rice. The present compound, therefore, is useful as fungicide for agricultural and horticultural crops, particularly for crops such as rice, wheat and barley, corn, sugar cane, cotton, beans, and grape. It has, moreover, sterilizing effect on seeds.

The present compound is effective in controlling plant diseases as mentioned above, exhibiting a strong fungicidal activity and a broad antifungal spectrum. Being penetrative into the plant body, the present compound permits of disease control not only by spraying but also by treatment of submerged paddy, or of soil; after application it remains active over a long period of time and hardly produces harmful side effects on useful crops.

The agricultural and horticultural fungicide as herein referred to is a controlling agent for preventing or curing the diseases of agricultural and horticultural crops including food crops such as rice, wheat and barley, and beans; industrial crops such as mulberry, tobacco, cotton, and sesame; fruit trees, vegetables, and ornamental plants.

The present compound is a novel compound having a melting point of 95° - 97° C which can be synthesized by the method disclosed below.

Synthesis of the present compound can be carried out in an inert solvent by reacting o-trifluoromethylbenzoyl chloride with m-isopropoxyaniline in the presence of a base, as shown in the following scheme:

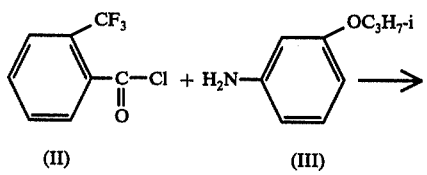

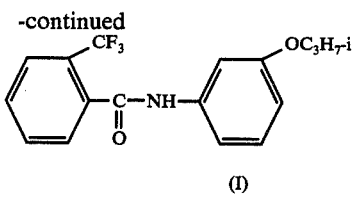

(I)

Examples of the inert solvents used in the synthesis include aromatic hydrocarbons such as benzene, toluene and xylene; chloroalkanes such as dichloromethane, chloroform and carbon tetrachloride; ketones such as acetone, methyl ethyl ketone and cyclohexanone; ethers such as diethyl ether, dioxane and tetrahydrofuran; and lower fatty acids such as acetic acid. Of these, benzene and tetrahydrofuran are preferred.

The bases suitable for use are organic amines such as trimethylamine, triethylamine, diethylaniline and pyridine, and inorganic bases such as potassium carbonate, sodium carbonate, sodium hydrogencarbonate, potassium hydrogencarbonate, sodium hydroxide and potassium hydroxide.

In carrying out the reaction, the amount of m-isopropoxyanilien used for 1 mole of o-trifluoromethylbenzoyl chloride is suitably selected from the range of 1 to 1.5 moles, preferably 1 to 1.2 moles and the amount of base from the range of 1 to 1.5 moles, preferably 1 to 1.2 moles, though the ratios are not necessarily limited to said ranges.

The reaction temperature is suitably selected from the range of −5° C to the boiling point of the solvent employed.

In applying the present compound as an agricultural and horticultural fungicide, it is used in the form convenient for application, as in the case of conventional agricultural chemicals. The present compound can be formulated into fungicidal compositions by use of suitable inert carriers and, if necessary, adjuvants in suitable ratios. The resulting composition is dissolved, dispersed, suspended, mixed, impregnated, adsorbed, or adhered to form a suitable preparation such as, for example, suspension, emulsifiable concentrate, solution, wettable powder, dust, granule, or tablet.

The inert carriers to be used with the present compound can be in the form of either solid or liquid. Examples of the solid carriers include powders of vegetable origin such as soybean flour, cereal meals, wood flour, bark flour, saw dust, ground tobacco plant stalk, walnut shell meal, bran, powdered cellulose, and extraction residues of vegetable substances; fibrous products such as paper, corrugated fiberboard, and old rags; synthetic polymers such as ground synthetic resins; powdered inorganic substances including clays such as, for example, kaolin, bentonite, and acid clay, talcs such as, for example, talc and pyrophyllite, siliceous materials such as, for example, diatomaceous earth, siliceous sand, mica, and "white carbon" (a synthetic high-dispersion silicic acid, often called finely powdered hydrated silica or hydrated silicic acid; there is also a product containing calcium silicate as major component) and other powdered inorganic products such as activated carbon, powdered sulfur, pumice stone, calcined diatomaceous earth, ground brick, fly ash, sand, calcium carbonate, calcium phosphate, and Glauber's salt; compost and chemical fertilizers such as ammonium sulfate, ammonium phosphate, ammonium nitrate, urea, and ammonium chloride. These substances are used each alone or in combinations of two or more.

The substance usable as liquid carrier is selected from those having solvent power by itself toward the present compound and those which are non-solvent by itself but are able to disperse the present compound by the aid of adjuvant. Examples of these carrier liquids, which are used each alone or in combinations of two or more, include water, alcohols such as, for example, methanol, ethanol, isopropanol, butanol, and ethylene glycol; ketones such as, for example, acetone, methyl ethyl ketone, methyl isobutyl ketone, diisobutyl ketone, and cyclohexanone; ethers such as, for example, ethyl ether, dioxane, Cellosolves, dipropyl ether, and tetrahydrofuran; aliphatic hydrocarbons such as, for example, gasoline and mineral oils; aromatic hydrocarbons, such as, for example, benzene, toluene, xylenes, solvent naphtha, and alkylnaphthalenes; halohydrocarbons such as, for example, dichloroethane, chlorobenzene, chloroform, and carbon tetrachloride; esters such as, for example, ethyl acetate, dibutyl phthalate, diisopropyl phthalate, and dioctyl phthalate; acid amides such as, for example, dimethylformamide, diethylformamide, and dimethylacetamide; nitriles such as, for example, acetonitrile; and dimethyl sulfoxide.

The adjuvants listed below are used in accordance with the object of their addition. They are used, sometimes, in combinations of two or more; in some cases, no adjuvant is used.

For the purpose of emulsifying, dispersing, solubilizing, or wetting the active compound, a surface active agent is used. Examples of such active agents include polyethylene alkylaryl ethers, polyoxyethylene alkyl ethers, polyoxyethylene higher fatty acid esters; polyoxyethylene resin acid esters, polyoxyethylene sorbitan monolaurate, polyoxyethylene sorbitan monooleate, alkylarylsulfonic acid salts, naphthalenesulfonic acid condensates, ligninsulfonic acid salts, and higher alcohol sulfate esters. For the purpose of stabilizing the dispersion of the active compound and tackifying and/or binding the active compound, there are used adjuvants such as, for example, casein, gelatin, starch, alginic acid, methylcellulose, carboxymethylcellulose, gum arabic, polyvinyl alcohol, turpentine oil, rice bran oil, bentonite, and ligninsulfonates.

To improve the flow property of a solid preparation, there may be used waxes, stearate salts, and alkyl phosphates. Naphthalenesulfonic acid condensates and polyphosphate salts are used as peptizer in a preparation of the suspension type. It is also possible to incorporate a defoamer such as silicone oil.

The active compound content of the fungicidal composition can be adjusted to meet the requirement. A suitable content is usually 0.5 to 20% by weight for dust or granule and 10 to 50% by weight for emulsifiable concentrate or wettable powder.

To prevent or cure the agricultural or horticultural plant diseases, an effective amount of the fungicidal preparation of this invention is applied as such or after suitably diluted with or suspended in water or other media to the plant or to the surroundings of the plant. Thus, the present invention includes in its scope the modes of preventive and curing application of the compound directly to the exposed portion of the plant above the soil or through the soil to the plant.

The amount to be applied of the present fungicidal preparations depends upon a variety of factors such as, for example, type of the disease to be treated, degree of the damage, tendency of the occurrence of the disease, climatic and environmental conditions, and type of the preparation. When emulsifiable concentrates or wettable powders are used, the final concentration of the active compound in a fungicidal liquir ready for application is at least 0.001% by weight in actual practice. In the case of dusts or granules, the application rate is suitably selected from the range of 30 to 600 g in terms of active compound per 10 ares.

The present compound can be applied cojointly or in mixtures with other agricultural chemicals, fertilizers, and plant nutrients which are applicable simultaneously with the present compound. Thus, the present compound can be applied in the form of multipurpose controlling agent by admixing with other agricultural chemicals for controlling diseases and pests of the objective crop, which are to be applied on the same occasion as that of applying the present fungicidal preparation for the preventive or curing purpose.

Typical examples of the agricultural chemicals used in the above multipurpose preparations include synthetic fungicides such as blastcidin S, kasugamicin, other antibiotics, O,O-diisopropyl S-benzyl thiophosphate, O-ethyl S,S-diphenyl dithiophosphate, 4,5,6,7-tetrachlorophthalide, diisopropyl, 1,3-dithiolan-2-ylidene malonate, methyl-1-(butylcarbamoyl)-2-benzimidazole carbamate, N-trichloromethylthio-4-cyclohexene-1,2-dicarboxyimide, 5-ethoxy-3-trichloromethyl-1,2,4-thiodiazole; organophosphorus insecticides such as O,O-dimethyl-O-(3-methyl-4-nitrophenyl)phosphorothioate, O-ethyl-O-p-nitrophenyl phenylphosphonothioate, O,O-dimethyl-S-(1,2-dicarbethoxyethyl)phosphorodithioate, dimethyl-(2,2,2-trichloro-1-hydroxyethyl)phosphonate; carbamate insecticides such as 1-naphthyl-N-methylcarbamate, m-tolyl-N-methylcarbamate, 2-sec-butylphenyl-N-methylcarbamate; N,N-dimethyl-N'-(2-methyl-4-chlorophenyl)formamidine hydrochloride, 1,3-bis(carbamoylthio)-2-(N,N-dimethylamino)propane hydrochloride.

The invention is illustrated below in detail with reference to Examples, in which all parts are by weight.

EXAMPLE 1

Synthesis of o-trifluoromethyl-m'-isopropoxybenzoic anilide.

To a tetrahydrofuran solution containing 1.5 g (0.01 mole) of m-isopropoxyaniline and 1.2 g (0.011 mole) of triethylamine, while being cooled in ice water, was added slowly 2.3 g (0.011 mole) of o-trifluoromethylbenzoyl chloride. After having been stirred for 2 hours at room temperature, the reaction mixture was freed from triethylamine hydrochloride by filtration and then from the solvent by distillation under reduced pressure. The residue was recrystallized from n-hexane to obtain 2.9 g (91% yield) of the intended product melting at 95° to 97° C.

EXAMPLE 2

A granule preparation was obtained by uniformly mixing the following ingredients, then thoroughly kneading with a suitable amount of water, and granulating:

| | |
|---|---|
| compound of this invention | 5 parts |
| bentonite-clay mixture containing major quantity of bentonite | 90 parts |
| calcium ligninsulfonate | 5 parts |

EXAMPLE 3

An emulsifiable concentrate was prepared by mixing the following ingredients to form a uniform solution:

| | |
|---|---|
| compound of this invention | 20 parts |
| tetrahydrofuran | 20 parts |
| xylene | 45 parts |
| a mixture of polyoxyethylene nonylphenyl ether and sodium alkylbenzenesulfonate | 15 parts |

EXAMPLE 4

A wettable powder preparation was obtained by uniformly mixing and grinding the following ingredients:

| | |
|---|---|
| compound of this invention | 50 parts |
| diatomaceous earth-clay mixture | 45 parts |
| polyoxyethylene nonylphenyl ether | 5 parts |

EXAMPLE 5

A dust preparation was obtained by uniformly mixing and grinding the following ingredients:

| | |
|---|---|
| compound of this invention | 4 parts |
| diatomaceous earth-clay-talc mixture | 95 parts |
| calcium stearate | 1 part |

Test Examples are given below to demonstrate the effectiveness of the present compound.

TEST EXAMPLE 1

Test of the antifungal activity of the compound of this invention toward various pathogenic fungi.

Method for testing antifungal activity: The test fungus was inoculated into a potato-agar medium treated with a test sample of the fungicidal preparation of the predetermined concentration, in a Petri dish, 9 cm in diameter. Incubation was continued until the diameter of the mycelium in a control dish had reached 9 cm. Percentage growth inhibition was calculated using the following equation:

$$\text{Percentage inhibition} = \frac{\left(\begin{array}{c}\text{Dia. of mycelium}\\ \text{in control dish}\end{array}\right) - \left(\begin{array}{c}\text{Dia. of mycelium}\\ \text{in treated dish}\end{array}\right)}{\left(\begin{array}{c}\text{Dia. of mycelium}\\ \text{in control dish}\end{array}\right)} \times 100$$

Table 1.
Results of antifungal activity test

| Test fungus | Percentage growth inhibition (%) | | |
|---|---|---|---|
| | 10 ppm | 5 ppm | 1 ppm |
| Sclerotinia mali | | | 100 |
| Corticium rolfsii | 100 | 83 | 67 |
| Pellicularia filamentosa | | 100 | 94 |
| Rhizoctonia solani IA | | 100 | 31 |
| Rhizoctonia solani IB | | 100 | 79 |
| Rhizoctonia solani II | | | 100 |
| Rhizoctonia solani IIIA | | 100 | 67 |
| Rhizoctonia solani IIIB | | 100 | 63 |
| Rhizoctonia solani IV | | 100 | 24 |
| Sclerotium orizicola | 100 | 90 | 72 |

TEST EXAMPLE 2

Test of the effectiveness in controlling rice sheath blight (pot test).

The test sample of the predetermined concentration was sprayed by means of a spray gun (1.5 kg/cm²) on greenhouse-grown paddy rice ("Jikkoku" variety; about 20 cm in height) planted in a pot on a turntable, the application rate having been 10 ml per pot. After one day and five days, a rice sheath blight fungus cultivated on rice straw was inoculated into the basal parts of riceplant tiller. Five days and 10 days after inoculation, the length of the developed disease spot was measured to obtain the total length (cm) of disease spots per stem. The control value was calculated by means of the following equation:

$$\text{Control value (\%)} = \frac{\left(\begin{array}{c}\text{Disease spot}\\ \text{length per stem}\\ \text{in control pot}\end{array}\right) - \left(\begin{array}{c}\text{Disease spot}\\ \text{length per stem}\\ \text{in treated pot}\end{array}\right)}{\left(\begin{array}{c}\text{Disease spot length}\\ \text{per stem in control pot}\end{array}\right)}$$

The results obtained were as shown in Table 2.

Table 2

| Test preparation | Concentration of active compound (ppm) | Control value (%) after | |
|---|---|---|---|
| | | 5 days | 10 days |
| Present compound | 400 | 100 | 100 |
| | 200 | 100 | 100 |
| (CF₃ / C(=O)NH / OC₃H₇-i) | 100 | 100 | 100 |
| | 50 | 94 | 90 |
| | 25 | 90 | 80 |
| Reference compound A | 400 | 100 | 95 |
| | 200 | 100 | 60 |
| (CH₃ / C(=O)NH / OC₃H₇-i) | 100 | 85 | 40 |
| | 50 | 70 | 32 |
| | 25 | 55 | 18 |
| Reference compound B | 200 | 20 | 10 |
| (CF₃ / C(=O)NH / OCH₃) | | | |
| Reference compound C | 200 | 16 | 7 |

Table 2-continued

| Test preparation | Concentration of active compound (ppm) | Control value (%) after 5 days | Control value (%) after 10 days |
|---|---|---|---|
| Reference compound D (CF₃—C₆H₄—C(=O)—NH—C₆H₄—OC₃H₇-i) | 100 | 3 | 1 |
| | 200 | 18 | 10 |
| Reference compound E (CF₃—C₆H₄—C(=O)—NH—C₆H₄—OC₃H₇-i) | 100 | 0 | 0 |
| | 200 | 22 | 15 |
| (CF₃—C₆H₄—C(=O)—NH—C₆H₄—OC₃H₇-i) | 100 | 9 | 3 |
| Validamycin (Commercial antibiotic preparation) | 30 | 80 | 60 |
| Control | — | 0 | 0 |

TEST EXAMPLE 3

Test of effectiveness in controlling rice sheath blight by the application to submerged application into paddy field.

The water in a pot, 8.5 cm in diameter, which was planted with paddy rice plant grown to a height of about 20 cm, was applied with 50 ml of the test preparation diluted to a predetermined concentration. After the pot had been left in a greenhouse for 5 days, a rice sheath blight fungus cultivated on rice hull-rice bran for 6 to 7 days was inoculated into the basal parts of the riceplant tiller. Five days after inoculation, the length of the developed disease spot of sheath blight was measured and the control value was calculated using the equation given in Test Example 2. The results obtained were as shown in Table 3.

Table 3

| Test preparation | Concentration of active compound (g/10 ares) | Control value (%) |
|---|---|---|
| Present compound (CF₃—C₆H₄—C(=O)—NH—C₆H₄—OC₃H₇-i) | 500 | 98 |
| | 250 | 97 |
| | 125 | 99 |
| Reference compound A (CH₃—C₆H₄—C(=O)—NH—C₆H₄—OC₃H₇-i) | 500 | 40 |
| | 250 | 17 |
| | 125 | 20 |
| Control | — | 0 |

TEST EXAMPLE 4

Effectiveness in controlling cucumber damping-off.

The fungicidal preparation of the predetermined concentration was applied over 20 cucumber seedlings (variety: "Ochiai") in cotyledonous stage which were planted in an unglazed pot, 16.5 cm in diameter, by means of a spray gun at a rate of 3 liters/m². After the solution adhered to the seedlings had been dried, a damping-off fungus (Rhizoctonia solani IB) cultivated on bran was inoculated on the soil surface. The test was repeated three times. Four days after the inoculation, inspection was performed and percentage disease seedling as well as percentage healthy seedling were calculated in the following way:

$$\text{Percentage disease seedling} = \frac{\text{Number of diseased seedlings in test pot}}{\text{Number of inspected seedlings in test pot}} \times 100$$

$$\text{Percentage healthy seedling} = \frac{\text{Number of healthy seedlings in test pot}}{\text{Number of inspected seedlings in test pot}} \times 100$$

Table 4
Effectiveness in controlling cucumber damping-off

| Test preparation | Amount applied (active component g/m²) | Percentage disease seedling | Percentage healthy seedling |
|---|---|---|---|
| Present compound | 2 | 0.0 | 100 |
| | 1 | 9.6 | 80.4 |
| | 0.5 | 27.8 | 72.2 |
| Reference compound C 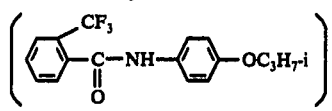 | 2 | 85.6 | 12.1 |

Table 4-continued

| Test preparation | Effectiveness in controlling cucumber damping-off | | |
|---|---|---|---|
| | Amount applied (active component g/m²) | Percentage disease seedling | Percentage healthy seedling |
| Reference compound D 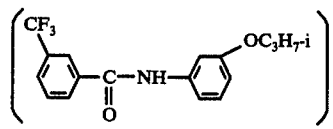 | 2 | 83.2 | 12.4 |
| Reference compound B 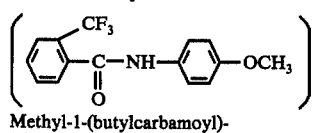 | 2 | 86.1 | 13.9 |
| Methyl-1-(butylcarbamoyl)-2-benzimidazole carbamate | 2 | 80.0 | 20.0 |
| Control | — | 88.3 | 11.0 |

TEST EXAMPLE 5

Activity against cucumber southern blight.

The fungicidal preparation of the predetermined concentration was applied over 20 cucumber seedlings (variety: "Ochiai") in seed leaf stage which were planted in an unglazed pot, 16.5 cm in diameter, by means of a spray gun at a rate of 3 liters/m². After the solution adhered to the seedlings had been dried, a sourthern blight fungus (Corticium rolfsii) cultivated on bran was inoculated on the soil surface. The test was repeated three times. Four days after the inoculation, inspection was performed and percentage disease seedling as well as percentage healthy seedling were calculated.

$$\text{Percentage disease seedling} = \frac{\text{Number of diseased seedlings in test pot}}{\text{Number of inspected seedlings in test pot}} \times 100$$

$$\text{Percentage healthy seedling} = \frac{\text{Number of healthy seedlings in test pot}}{\text{Number of inspected seedlings in test pot}} \times 100$$

Table 5

| Test preparation | Activity against cucumber southern blight | | |
|---|---|---|---|
| | Amount applied (active component g/m²) | % Disease seedling | % Healthy seedling |
| Present compound | 2 | 5.1 | 94.9 |
| | 1 | 5.1 | 94.9 |
| | 0.5 | 12.5 | 87.5 |
| Reference compound C 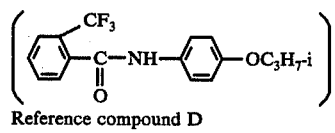 | 2 | 88.6 | 11.4 |
| Reference compound D 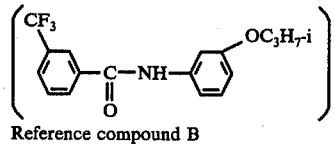 | 2 | 92.3 | 7.7 |
| Reference compound B 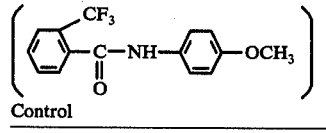 | 2 | 94.6 | 5.4 |
| Control | — | 100 | 0 |

TEST EXAMPLE 6

Activity against crown rust of oat

The fungicidal preparation of a predetermined concentration (50 ml/pot) as sprayed over oat seedlings in four-leaf stage, planted in a pot, 9 cm in diameter. Immediately after the sprayed preparation had been air-dried, a crown rust fungus (Puccinia coronate) was inoculated. The control value was calculated using the followng equation from the inspection results obtained after two weeks from the inoculation.

$$\text{Control value (\%)} = \frac{X - Y}{X} \times 100$$

where
X: Number of disease spots per leaf in control pot,
Y: Number of disease spots per leaf in test pot.

Table 6

| Test preparation | Activity against oat crown rust Concentration (ppm) | Number of disease spots per leaf | Control value (%) |
| --- | --- | --- | --- |
| Present compound | 1000 | 1.7 | 97.5 |
|  | 500 | 4.7 | 93.0 |
| Reference compound C | 1000 | 54.2 | 18.9 |
| 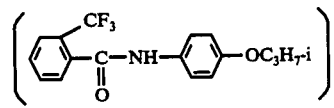 | | | |
| Reference compound D | 1000 | 58.1 | 13.1 |
| 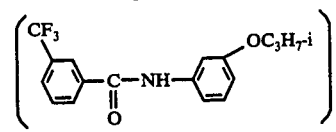 | | | |
| Reference compound B | 1000 | 61.3 | 8.2 |
| 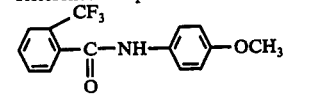 | | | |
| Control | | 66.8 | 0 |

What is claimed is:

1. The benzoic anilide derivative represented by the structural formula (I):

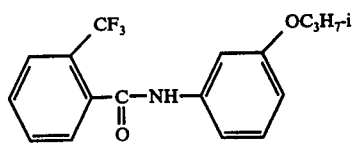 (I)

2. An agricultural and horticultural fungicidal composition comprising a fungicidally effective amount of the compound represented by the structural formula (I), an active ingredient and an inert diluent.

3. A method for controlling fungal diseases of agricultural and horticultural crops, which comprises applying to said crops a fungicidally effective amount of the compound represented by the structural formula (I),

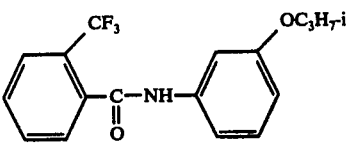 (I)

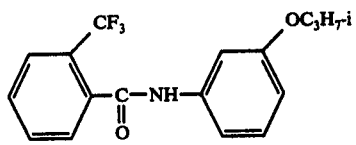 (I)

* * * * *